United States Patent [19]

Ball et al.

[11] 4,327,190

[45] Apr. 27, 1982

[54] PROCESS FOR THE PRODUCTION OF $C_1$ TO $C_4$ OXYGENATED HYDROCARBONS

[75] Inventors: William J. Ball, Capel; Leonard Cotton, Ewell; David G. Stewart, Epsom, all of England

[73] Assignee: The British Petroleum Company Limited, London, England

[21] Appl. No.: 141,560

[22] Filed: Apr. 18, 1980

[30] Foreign Application Priority Data

Apr. 24, 1979 [GB] United Kingdom ............... 14253/79

[51] Int. Cl.[3] ............................................. C07C 27/06

[52] U.S. Cl. .................................... 518/714; 518/701; 518/716

[58] Field of Search ........................ 260/449 R, 449.5; 518/714, 716, 701

[56] References Cited

U.S. PATENT DOCUMENTS 4,096,164 6/1978 Ellgen et al. .................. 260/449 R 4,224,236 9/1980 Wunder et al. ................. 260/449 R

*Primary Examiner*—Howard T. Mars

*Attorney, Agent, or Firm*—Brooks, Haidt, Haffner & Delahunty

[57] ABSTRACT

Oxygenated hydrocarbon compounds containing from one to four carbon atoms, e.g. acids, alcohols and/or aldehydes are produced by reacting carbon monoxide with hydrogen in the presence of a supported mixture of a rhodium component and a chromium component, optionally incorporating also iron, manganese, molybdenum, tungsten or ruthenium at elevated temperature and generally at elevated pressure. A preferred support is silica which may be activated by the addition of metal and non-metal activators followed by calcination, prior to incorporation of the rhodium and chromium components.

9 Claims, 1 Drawing Figure

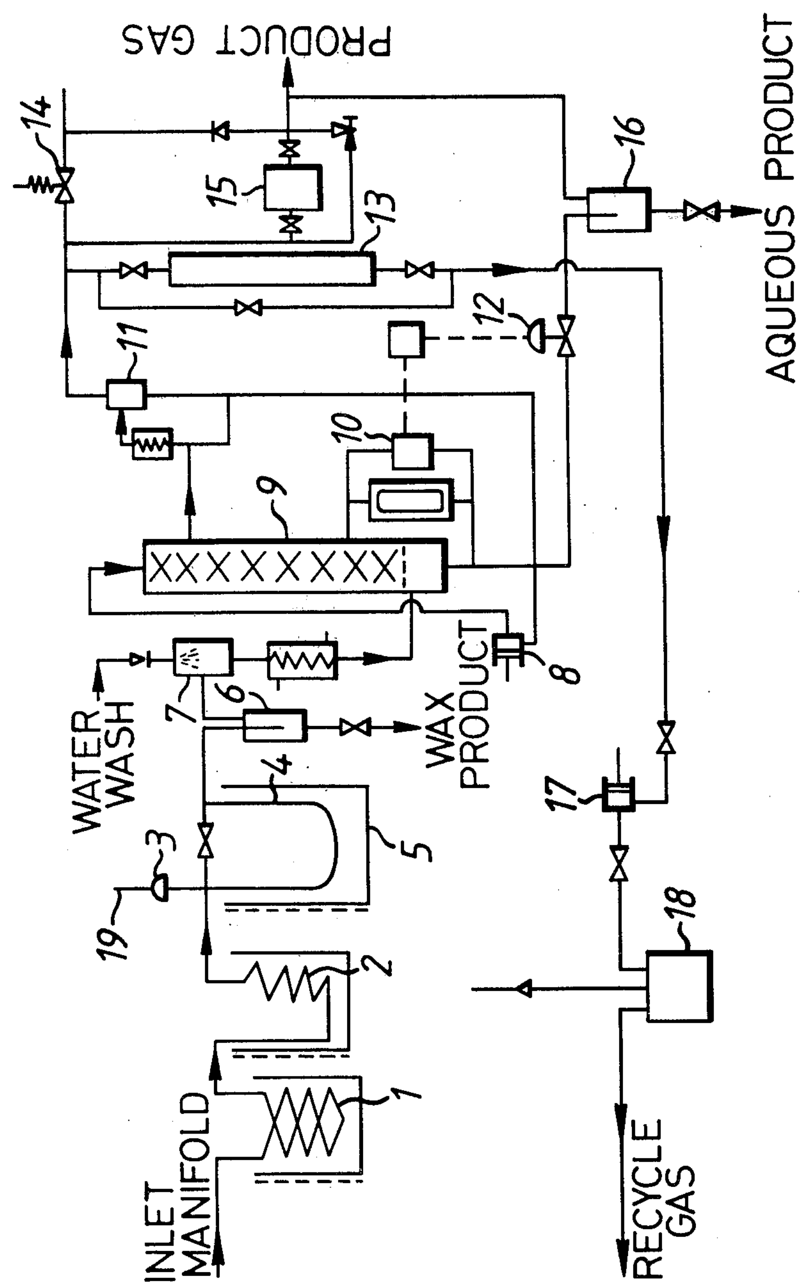
PRODUCT GAS
AQUEOUS PRODUCT
WATER WASH
WAX PRODUCT
INLET MANIFOLD
RECYCLE GAS
1
2
3
4
5
6
7
8
9
10
11
12
13
14
15
16
17
18
19

PROCESS FOR THE PRODUCTION OF $C_1$ TO $C_4$ OXYGENATED HYDROCARBONS

The present invention relates generally to a process for the production of $C_1$ to $C_4$ oxygenated hydrocarbon compounds such as acids, alcohols and/or aldehydes.

$C_2$-oxygenated hydrocarbons such as acetic acid, ethanol and acetaldehyde are valuable industrial products. On a commercial scale acetic acid is generally produced either by oxidation of paraffinic hydrocarbon fractions or by carbonylation of methanol; ethanol is produced either by fermentation of natural products, e.g. molasses or by hydration of ethylene in the presence of an acid catalyst; acetaldehyde is produced by the oxidation of ethanol or by direct oxidation of ethylene as in the Wacker process. $C_3$ and $C_4$ acids, alcohols and aldehydes are produced from petrochemical feedstocks by similar processes involving oxidation, hydroformylation, hydrogenation and hydration. The dwindling reserves of crude oil from which many of the above feedstocks are derived and the associated need to utilise fully the remaining natural resources such as coal and the vast amounts of gases, e.g. methane potentially available from the exploitation of North Sea oilfields, has stimulated research into the utilisation of mixtures of carbon monoxide and hydrogen, hereinafter to be referred to as synthesis gas, which can readily be obtained not only from crude oil but also from both coal and methane gas. Much of the early work on synthesis gas conversion involved the use as catalysts of the metals of Group VIII of the Periodic Table such as iron, cobalt, nickel and ruthenium and various other metal oxide systems. One general disadvantage of such systems is that catalysts which possess acceptable activity generally tend to be unselective ie they produce a wide spectrum of products including both hydrocarbons and oxygenated hydrocarbons having a very broad distribution of carbon numbers. This not only complicates the recovery of the desired products but also results in the wastage of reactants to undesirable products. On the other hand those catalysts having acceptable selectivity generally have a low activity thereby necessitating recycle of large quantities of unchanged reactants.

In U.S. application Ser. No. 541,661 (Union Carbide Corp.) there is disclosed a process which, it is claimed, overcomes the aforesaid disadvantages of the prior art processes. The process for selectively producing $C_2$-oxygenated hydrocarbons involves continuously contacting synthesis gas with a heterogeneous catalyst essentially comprising rhodium metal under reaction conditions correlated so as to favour the formation of a substantial proportion of acetic acid, ethanol and/or acetaldehyde. Subsequent patent applications describe the production of ethanol and/or acetic acid by contacting synthesis gas with a rhodium/iron catalyst (U.S. Ser. No. 541,660), a rhodium/manganese catalyst (DT No. 2,628,463), a rhodium/molybdenum or rhodium/-tungsten catalyst (U.S. Pat. No. 4,096,164) and a rhodium/ruthenium catalyst (U.S. Pat. No. 4,101,450).

It has now been found that a supported mixture of a rhodium component and a chromium component is an active catalyst for the selective production of oxygenated hydrocarbon compounds containing from one to four carbon atoms.

Accordingly the present invention provides a process for the production of oxygenated hydrocarbon compounds containing from one to four carbon atoms which process comprises contacting synthesis gas with a catalyst comprising a supported mixture of a rhodium component and a chromium component under reaction conditions which favour the formation of acids, alcohols and/or aldehydes.

Mixtures of the gases hydrogen and carbon monoxide are abundantly available in the form of synthesis gas. Methods for preparing synthesis gas are well-known in the art and usually involve the partial oxidation of a carbonaceous substance, eg coal. Alternatively synthesis gas may be prepared, for example, by the catalytic steam reforming of methane. Although it is preferred to use substantially pure synthesis gas the presence of such impurities as carbon dioxide and nitrogen can be tolerated. On the other hand impurities which have a deleterious effect on the reaction should be avoided. The ratio of hydrogen to carbon monoxide in the synthesis gas may vary widely. Normally the molar ratio of hydrogen to carbon monoxide may be in the range of from 20:1 to 1:20, preferably from 5:1 to 1:5. Methods for adjusting the molar ratio of hydrogen to carbon monoxide by the so-called 'shift reaction' are well-known to those versed in the art.

The catalyst comprises a supported mixture of a rhodium component and a chromium component. A wide variety of support materials may be employed. Suitable support materials include silica, alumina, silica/alumina, magnesia, thoria, titania, chromia, zirconia and active carbon, of which silica is preferred. Zeolite molecular sieves and in particular the crystalline zeolites may also be employed. Suitably the support has a relatively high surface area. The support may have a surface area up to 350 square meters per gram (BET low temperature nitrogen adsorption isotherm method), preferably in the range 1 to 300 square meters per gram. Whilst the actual form of the rhodium and chromium components under the reaction conditions is not known with any degree of certainty it is likely that they are in either the oxide form or in the metallic form under the reducing conditions prevailing. Thus the rhodium and chromium components may be added in the form of the metals themselves or in the form of metal compounds and may be added concurrently or sequentially. The rhodium and chromium components may be deposited on the support by any of the techniques commonly used for catalyst preparation. Although it is possible to add particles of the metals to the support it is preferred to use the techniques of impregnation from an organic or inorganic solution, precipitation, coprecipitation or cation exchange. Conveniently the catalyst may be prepared by impregnating the support with a solution of an inorganic or organic rhodium and chromium compound. Suitable compounds are the salts of the metals, e.g. the halides, particularly the chlorides and nitrates. Following impregnation the catalyst is preferably dried and calcined. The amount of each of the rhodium component and the chromium component on the support may suitably be in the range of from 0.01 to 25 weight percent, preferably from 0.1 to 10 weight percent, based on the combined weight of the metals and the support. The catalyst may be further improved by incorporating one or more other metal components selected from iron, manganese, molybdenum, tungsten and ruthenium. Each additional metal component may be present in an amount in the range from 0.1 to 10 weight percent based on the combined weight of the metals and the support.

In another embodiment of the present invention the support can be activated by the addition of one or more metal or non-metal activator components followed by calcination prior to incorporation of the rhodium and chromium components and, optionally, other metals. Whilst a wide variety of such metals and non-metals may be added, the alkali metals, thorium, manganese, rhodium, iron, chromium, molybdenum, boron and phosphorus are specific examples of such materials. Any of the known techniques for catalyst preparation hereinbefore referred to may be used for addition of the activating material. In the case of a metal activator the support is preferably impregnated with a solution of a compound of the metal, suitably the nitrate or chloride, and is thereafter dried, suitably by evaporation and calcined. The activated support is then in a suitable condition for addition of the rhodium and chromium components. The amount of activator component added may suitably be in the range 0.01 to 50 weight percent, preferably from 1 to 25 weight percent based on the combined weight of the activator component and the support.

With regard to the reaction conditions the temperature may suitably be in the range of from 150° to 450° C., preferably from 200° to 400° C. and even more preferably from 220° to 350° C.; the use of higher temperatures within the aforesaid ranges tends to increase the co-production of methane. Because of the highly exothermic nature of the reaction the temperature requires careful control in order to prevent a runaway methanation, in which methane formation increases with increasing temperature and the resulting exotherm increases the temperature still further. In fixed bed operations, temperature control may be achieved by mixing the catalyst with an inert diluent, thereby ensuring that the exothermic heat is more evenly distributed. In this way the useful life of the catalyst may be protected and prolonged. The reaction pressure is suitably in the range from 1 to 700 bar, preferably from 20 to 300 bar. The use of higher pressures within the aforesaid ranges increases the production rate and selectivity to $C_2$ to $C_4$ oxygenated hydrocarbons.

An important reaction parameter is the conversion. A low conversion, preferably less than 20% of the carbon monoxide, favours the formation of the lower acids, alcohols and aldehydes. A low conversion may suitably be achieved in a continuous process by employing a high space velocity. Suitably the gas hourly space velocity (volume of synthesis gas, at STP, per volume of catalyst per hour) is greater than $10^3$ per hour, preferably the gas hourly space velocity is in the range from $10^4$ to $10^6$ per hour. Excessively high space velocities result in an uneconomically low conversion while excessively low space velocities result in a loss of selectivity to desirable products.

Although the reaction may be carried out batchwise it is preferably carried out in a continuous manner.

The catalyst may be employed in the form of a fixed or a fluidised bed.

The effluent from the reaction may be freed from the desired oxygenated products by various means, such as scrubbing and/or distillation. The residual gas which consists mainly of unreacted synthesis gas may be mixed with fresh carbon monoxide and hydrogen to give the required reactor feed and this composite gas then recycled to the reactor inlet.

The process of the invention will now be illustrated by the following Examples and Comparison Tests and by reference to the accompanying FIGURE which is a simplified flow diagram of the apparatus employed.

With reference to the FIGURE, 1 is a preheater (150° C.), 2 is a preheater (200° C.), 3 is a bursting disc, 4 is a reactor, 5 is a salt pot, 6 is a knock-out pot, 7 is a water quench, 8 is a water recycle pump, 9 is a water wash tower, 10 is a DP level controller, 11 is a knock-out pot, 12 is a Foxboro vale, 13 is a molecular sieve dryer, 14 is a Gyp relief valve, 15 is a back pressure regulator, 16 is an aqueous product receiver, 17 is a gas recycle pump, 18 is a ballast vessel and 19 is a vent.

CATALYST PREPARATION

Catalyst A

Chromium/manganese/thorium/silica

Thorium nitrate hexahydrate (5 g) was dissolved in deionised water (20 ml) and added to Davison grade 59 silica (10 g, 8–16 mesh, granules). The mixture was evaporated to dryness on a steam-bath, dried at 120° C. for 16 hours and calcined in air at 400° C. for 4 hours.

Chromium nitrate monohydrate (3.8 g) and manganese acetate tetrahydrate (0.2 g) were dissolved in deionised water (20 ml) and the resulting solution added to the above modified support. The mixture was evaporated to dryness on a steam-bath and dried at 120° C. for 16 hours. The catalyst was then heated in hydrogen at 450° C. for 16 hours.

Catalyst B

Chromium/molybdenum/silica

Chromium nitrate monohydrate (3.8 g) and ammonium heptamolybdate tetrahydrate (0.42 g) were dissolved in deionised water (20 ml) and the resulting solution was added to Davison grade 59 silica (10 g). The mixture was evaporated to dryness on a steam-bath and dried at 120° C. for 16 hours. The catalyst was heated in hydrogen at 450° C. for 16 hours.

Catalyst C

Molybdenum/rhodium/silica

Ammonium heptamolybdate tetrahydrate (0.42 g) and rhodium trichloride trihydrate (0.65 g) were dissolved in deionised water (20 ml) and added to Davison grade 59 silica (10 g, 8–16 mesh granules). The mixture was evaporated to dryness on a steam-bath and dried at 120° C. for 16 hours. The catalyst was reduced in hydrogen at 450° C. for 5 hours.

Catalyst D

Rhodium/tungsten/silica

Ammonium tungstate, $(NH_4)_{10}W_{12}O_{41}.5H_2O$ (0.13 g) and rhodium trichloride trihydrate (0.65 g) were dissolved in deionised water (20 ml) and added to Davison, grade 59 silica (10 g, 8–16 mesh granules). The mixture was evaporated to dryness on a steam-bath and dried at 120° C. for 16 hours. The catalyst was reduced in hydrogen at 450° C. for 5 hours.

Catalysts A to D are not catalysts as used in the performance of the present invention because they are deficient in one or other of the essential components, chromium and rhodium.

Catalyst E

Chromium/rhodium/silica

Chromium nitrate monohydrate (3.8 g) and rhodium trichloride trihydrate (1.3 g) were dissolved in deionised water (20 ml) and added to Davison grade 59 silica (10 g, 8–16 mesh granules). The mixture was evaporated to dryness on a steam-bath and dried at 120° C.

for 16 hours. The catalyst was reduced in hydrogen at 450° C. for 5 hours.

Catalyst F

Chromium/rhodium/thorium/silica

Thorium nitrate hexahydrate (5 g) and chromium nitrate monohydrate (1.9 g) were dissolved in deionised water (20 ml) and the resulting solution added to Davison, grade 59 silica (10 g, 8–16 mesh granules). The mixture was evaporated to dryness on a steam-bath, dried at 120° C. for 16 hours, calcined in air at 400° C. for 4 hours and heated in hydrogen at 450° C. for 4 hours.

Chromium nitrate monohydrate (1.9 g) and rhodium trichloride trihydrate (1.3 g) were dissolved in deionised water (20 ml) and the resultant solution added to the above modified support. The mixture was evaporated to dryness on a steam-bath, dried at 120° C. for 16 hours and reduced in hydrogen at 450° C. for 5 hours.

Catalyst G

Chromium/Molybdenum/Rhodium/Silica

Chromium nitrate monohydrate (3.8 g), ammonium heptamolybdate tetrahydrate (0.42 g) and rhodium trichloride trihydrate (1.3 g) were dissolved in deionised water (20 ml) and the resulting solution added to Davison, grade 59 silica (10 g, 8–16 mesh granules). The mixture was evaporated to dryness on a steam-bath, dried at 120° C. for 16 hours and the catalyst reduced in hydrogen at 450° C. for 16 hours.

Catalyst H

Chromium/Molybdenum/Rhodium/Silica

Ammonium heptamolybdate tetrahydrate (0.42 g) was dissolved in deionised water (20 ml) and the solution added to Davison grade 59 silica (10 g, 8–16 mesh granules). The mixture was evaporated to dryness on a steam-bath and dried at 120° C. for 16 hours.

Chromium nitrate monohydrate (3.8 g) and rhodium trichloride trihydrate (0.65 g) were dissolved in deionised water (20 ml) and the resulting solution added to the above modified support. The mixture was evaporated to dryness on a steam-bath, dried at 120° C. for 16 hours and the catalyst reduced in hydrogen at 450° C. for one hour.

EXAMPLE 1

With reference to the accompanying FIGURE a mixture of carbon monoxide and hydrogen in a molar ratio of 1:1 was passed via the inlet manifold through the two preheater coils (1) and (2) maintained at 150° C. and 200° C. respectively in silicone oil baths. The heated gases were then fed via a heat-traced line to the copper-lined reactor (4) containing a fixed bed of Catalyst E in the form of 8 to 16 mesh (BSS) granules. The reactor was maintained at the desired reaction temperature by immersion in a molten salt bath (5). The product gases were passed via a heat-traced line through a knock-out pot for wax products (6) to a small quench vessel (7) into the top of which water was sprayed. The gases were then passed through a water cooler to the bottom of the water wash tower (9) which was packed with ⅜ inch Raschig rings. In the tower (9) the product gases were washed counter-current with water. The resulting liquid product was fed into the receiver (16) and any dissolved gases were recombined with the product gas stream from the back pressure regulator (15). The separated gas stream from the top of the water wash tower (9) was passed through a water cooler to the knock-out pot (11) and then to the inlet side of the dome-loaded back pressure regulator (15). Recycle gas was recovered from the inlet side of the back pressure regulator (15), passed through a molecular sieve drier (13) and compressed up to 67 bars in the gas ballast vessel (18) using the gas recycle pump (17). The recycle gas was fed back to the inlet manifold. Provision was made to feed spot samples of the inlet gases and the total gas stream to a gas chromatographic analytical unit.

The product gas stream leaving the back pressure regulator (15) was measured and samples were withdrawn and analysed by gas chromatography. The liquid product was also sampled and analysed by gas chromatography.

After the reactor had reached equilibrium a balance run was carried out over a one hour period at a temperature of 250° C. Further runs were then carried out at 270° C. and 280° C. The results are given in the following Table.

EXAMPLE 2

The procedure of Example 1 was followed using Catalyst F in place of Catalyst E and no run was carried out at 260° C. Instead a run at 270° C. was repeated changing the GHSV to 24000. The results are given in the following Table.

EXAMPLE 3

The procedure of Example 1 was followed using Catalyst G in place of Catalyst E and the runs were carried out at 226° C. and 236° C. The results are given in the following Table.

EXAMPLE 4

The procedure of Example 1 was followed except that Catalyst H was used in place of Catalyst E and the runs were carried out at 260° C. and 275° C.

COMPARISON TEST 1

The procedure of Example 1 was followed except that Catalyst E was replaced by Catalyst A and the reaction temperature was 347° C. The results are given in the following Table.

COMPARISON TEST 2

The procedure of Example 1 was followed except that Catalyst E was replaced by Catalyst B and the runs were carried out at 315° C. and 374° C. The results are given in the following Table.

COMPARISON TEST 3

The procedure of Example 1 was followed except that Catalyst E was replaced by Catalyst C and the runs were carried out at 280° C., 290° C. and 300° C. The results are given in the following Table.

COMPARISON TEST 4

The procedure of Example 1 was followed except that Catalyst E was replaced by Catalyst D and the runs were carried out at 250° C., 260° C. and 270° C. The results are given in the following Table.

Comparison Tests 1 to 4 are not examples of the process of the present invention because the catalysts employed did not contain chromium and rhodium as essential components. They are included for the purpose of Comparison only.

TABLE

Reaction parameters: GHSV = 48,000; $H_2$:CO molar ratio = 1:1; Pressure = 50 bar; Recycle gas ratio = 20:1

| Example | Catalyst | Reaction Temp (°C.) | CO Conversion[1] (%) | SELECTIVITY[2] (%) $CO_2$ | $CH_4$ | $>C_2$[3] | MeOH[4] | EtOH[5] | Acet[6] | nPrOH[7] | n-BuOH[8] | Acetic acid | Esters[9] |
|---|---|---|---|---|---|---|---|---|---|---|---|---|---|
| Comp Test 1 | A | 347 | 0.9 | 43.0 | 16.0 | — | 24.0 | 17.0 | — | — | — | — | — |
| Comp Test 2 | B | 315 | 2.2 | 33.3 | 17.3 | 8.2 | 29.2 | 11.9 | — | — | — | — | — |
| | | 374 | 6.1 | 39.9 | 32.3 | 8.8 | 6.1 | 3.0 | — | — | — | — | — |
| Comp Test 3 | C | 280 | 7.9 | 13.4 | 26.5 | 8.6 | 33.5 | 12.2 | 0.8 | 2.9 | 1.0 | 0.5 | 0.5 |
| | | 290 | 9.7 | 15.3 | 29.6 | 9.4 | 27.4 | 9.6 | 0.4 | 4.7 | 0.4 | 1.8 | 1.5 |
| | | 300 | 12.0 | 18.0 | 32.8 | 10.5 | 25.7 | 7.9 | 0.3 | 2.2 | 0.3 | 1.4 | 0.8 |
| Comp Test 4 | D | 250 | 1.6 | 15.3 | 25.8 | 6.1 | 7.3 | 31.9 | 13.5 | — | — | — | — |
| | | 260 | 4.5 | 29.8 | 50.4 | 5.4 | 3.4 | 9.0 | 2.1 | — | — | — | — |
| | | 270 | 16.6 | 33.2 | 61.6 | 1.9 | 0.5 | 2.3 | 0.7 | — | — | — | — |
| 1 | E | 250 | 3.1 | 2.6 | 40.1 | 1.9 | 5.4 | 25.8 | 23.9 | — | — | — | — |
| | | 270 | 7.9 | 2.9 | 33.9 | 2.6 | 3.8 | 22.4 | 15.4 | — | — | 11.2 | 7.6 |
| | | 280 | 9.8 | 3.2 | 42.1 | 3.3 | 3.4 | 19.3 | 13.0 | — | — | 7.5 | 8.2 |
| 2 | F | 250* | 2.4 | 13.5 | 38.2 | — | — | 30.3 | 18.1 | — | — | — | — |
| | | 270* | 4.3 | 8.0 | 49.0 | 1.9 | — | 27.6 | 13.6 | — | — | — | — |
| | | 270 | 8.7 | 8.3 | 37.0 | 2.3 | 3.6 | 24.5 | 6.9 | — | — | 3.9 | 13.4 |
| 3 | G | 226 | 13.3 | 8.4 | 22.3 | 6.1 | 39.0 | 16.3 | 0.3 | 4.4 | 0.8 | 0.3 | 2.2 |
| | | 236 | 20.5 | 9.4 | 21.2 | 5.5 | 36.6 | 18.6 | 0.2 | 4.2 | 0.7 | 0.3 | 3.1 |
| 4 | H | 260 | 6.9 | 19.8 | 13.4 | 6.8 | 44.7 | 15.5 | — | — | — | — | — |
| | | 275 | 11.1 | 22.4 | 18.8 | 9.7 | 37.2 | 11.9 | — | — | — | — | — |

In the above Table:

[1] $\text{CO Conversion} = \frac{\text{Moles of carbon monoxide consumed}}{\text{Moles of carbon monoxide fed}} \times 100$

[2] $\text{Selectivity} = \frac{\text{Moles of carbon monoxide converted to particular product}}{\text{Moles of carbon monoxide consumed}} \times 100$

[3] $>C_2$ = Hydrocarbons with carbon numbers greater than 2
[4] MeOH = Methanol
[5] EtOH = Ethanol
[6] Acet = Acetaldehyde
[7] n-PrOH = n-propanol
[8] n-BuOH = n-butanol
[9] Esters = Methyl and ethyl acetates
*GHSV = 24000

Reference to the Table shows that Catalysts A and B which do not contain rhodium are relatively inactive for the hydrogenation of carbon monoxide. Examples 1 to 4 in which Catalysts E, F, G and H are employed demonstrate the improved activity/selectivity of supported rhodium/chromium catalysts. With reference to Comparison Test 3 (supported rhodium/molybdenum catalyst) the catalyst is less active than the catalysts employed in the process of the invention. With reference to Comparison Test 4 (supported rhodium/tungsten catalyst) the catalyst either has lower activity and comparable selectivity or greater activity at much lower selectivity to desirable products than the catalysts used in the process of the invention.

We claim:

1. A process for the production of oxygenated hydrocarbon compounds containing from one to four carbon atoms which process comprises contacting synthesis gas at a temperature in the range of from about 150° to 450° C. and a pressure in the range of from about 1 to 700 bars with a catalyst comprising a supported mixture essentially consisting of rhodium and chromium metals, each of said metals being present in an amount in the range of from about 0.01 to 25 weight percent based on the combined weight of the metals and support.

2. A process according to claim 1 wherein the support is silica.

3. A process as defined in claim 1 or 2 wherein one or more materials selected from the group consisting of alkali metals, thorium, manganese, boron and phosphorus is added to a support, the material added support is then calcined and rhodium and chromium metals are then incorporated therein.

4. A process according to claim 3 wherein the material added is in the range of from about 1 to 25 weight percent based on the combined weight of the material(s) and the support.

5. A process according to either claim 1 wherein the amount of each of the rhodium and the chromium metals on the support is in the range from 0.1 to 10 weight percent based on the combined weight of the metals and the support.

6. A process according to claim 1 wherein there is also incorporated in the supported mixture one or more other metals selected from from the group consisting of iron, manganese, molybdenum, tungsten and ruthenium.

7. A process according to claim 1 wherein the temperature is in the range 200° to 400° C. and the pressure is in the range 20 to 300 bar.

8. A process according to claim 1 wherein the gas hourly space velocity is in the range from $10^4$ to $10^6$ per hour.

9. A process according to claim 1 when carried out in a continuous manner.

* * * * *